US008623506B2

(12) United States Patent
Chen

(10) Patent No.: US 8,623,506 B2
(45) Date of Patent: Jan. 7, 2014

(54) NON-COVALENTLY BONDING ANTI-MICROBIAL NANOPARTICLES FOR WATER SOLUBLE WOOD TREATMENT

(75) Inventor: Sung-Wei Chen, Las Vegas, NV (US)

(73) Assignee: Empire Technology Development LLC, Wilmington, DE (US)

( * ) Notice: Subject to any disclaimer, the term of this patent is extended or adjusted under 35 U.S.C. 154(b) by 59 days.

(21) Appl. No.: 13/389,586

(22) PCT Filed: Jun. 22, 2011

(86) PCT No.: PCT/US2011/041372
§ 371 (c)(1),
(2), (4) Date: Feb. 8, 2012

(87) PCT Pub. No.: WO2012/177247
PCT Pub. Date: Dec. 27, 2012

(65) Prior Publication Data
US 2012/0328894 A1   Dec. 27, 2012

(51) Int. Cl.
*B32B 5/16* (2006.01)
(52) U.S. Cl.
USPC ......... 428/403; 428/537.1; 427/212; 977/811
(58) Field of Classification Search
USPC ......... 428/403, 212, 537.1; 977/811; 427/212
See application file for complete search history.

(56) References Cited

U.S. PATENT DOCUMENTS

| 2003/0134137 | A1 | 7/2003 | Laks et al. |
| 2005/0255251 | A1 | 11/2005 | Hodge et al. |
| 2007/0089846 | A1 | 4/2007 | Kim |
| 2009/0197105 | A1 | 8/2009 | Buchholz et al. |
| 2010/0233245 | A1* | 9/2010 | Narayana ................. 424/443 |
| 2010/0272819 | A1 | 10/2010 | Engelhardt et al. |

FOREIGN PATENT DOCUMENTS

| EP | 2168737 | * | 3/2010 |
| EP | 2168737 | A1 | 3/2010 |
| WO | WO2009/129904 | A2 | 10/2009 |
| WO | WO2010/057114 | * | 5/2010 |
| WO | WO2010/057114 | A2 | 5/2010 |

OTHER PUBLICATIONS

International Search Report and Written Opinion of PCT/US2011/041372 dated Dec. 6, 2011.
Cosgrove, Growth of the plan cell wall, *Nat Rev Mol Cell Biol.* (Nov. 2005), 6(11):850-861 [Abstract].
Guo et al., Synthesis and Characterization of Poly(vinylpyrrolidone)-Modified Zinc Oxide Nanoparticles, *Chem Mater.* (2000), 12(8):2268-2274 [Abstract].
Heitner, Lignin and Lignans: Advances in Chemistry, *CRC Press* (Jun. 14, 2010) [Abstract].
Kasture et al., Multiutility sophorolipids as nanoparticle capping agents: synthesis of stable and water dispersible Co Nanoparticles, *Langmuir* (Nov. 6, 2007), 23(23):11409-11412 [Abstract].
Padmavathy et al., Enhanced bioactivity of ZnO nanoparticles—an antimicrobial study, *Sci Technol Adv Mater.* (2008), 9:035004 (pp. 1-7).
Sawai et al., Quantitative evaluation of antifungal activity of metallic oxide powders (MgO, CaO and ZnO) by an indirect conductimetric assay, *Journal of Applied Microbiology* (2004), 96:803-809.
Sjostrom, Wood Chemistry: Fundamentals and Aplications, $2^{nd}$ Ed., Academic Press (1993) [Abstract].
Wei et al., "Green" synthesis of starch capped CdS nanoparticles, *Colloids and Surfaces A: Physiocochem. Eng. Aspects* (Mar. 30, 2004), 247:125-127.
Wu et al., Chemical Synthesis of ZnO Nanocrystals, *Nanotechnology* (Sep. 2007), 6(5):497-503 [Abstract].
Yang, Synthesis and Characterization of Cyclodextrin Capped AU and AG Nanoparticles, A Thesis Submitted for the Degree of Master of Science, Department of Chemistry, National University of Singapore (2009).
You et al., Engineering the nanoparticle-biomacromolecule interface, *Soft Matter* (Dec. 7, 2005), 2:190-204.
Z-Mite Nanoparticles from American Elements, Los Angles, California (http://www.americanelements.com) [Printed from Internet Dec. 19, 2011).
Kim et al., Biopolymer templating as synthetic route to functional metal oxide nanoparticles and porous sponges, *Polym. Chem.* (Dec. 8, 2009), 1(3):272-275.
Schultz et al., Long-Term Outdoor Efficacy Trials of Wood Treated with Organic Biocides and Co-Added Non Biocidal Additives, *American Wood Protection Association*, $114^{th}$ Annual Meeting, vol. 104, May 18-20, 2008, pp. 96-102.
Yamaguchi, Silicic acid/boric acid complexes as ecologically friendly wood preservatives, *Forest Products Journal* (Jan. 2005), 55(1):88-92.
Wood Handbook: Wood as an Engineering Material, General Technical Report FPL-GTF-190, Forest Products Laboratory, U.S. Department of Agriculture, Forest Services, Madison, Wisconsin (Apr. 2010), pp. 1-509.

* cited by examiner

*Primary Examiner* — Leszek Kiliman
(74) *Attorney, Agent, or Firm* — Pepper Hamilton LLP

(57) ABSTRACT

Embodiments described herein include capped nanoparticles having a nanoparticle core and at least one capping agent including a biochemical constituent of wood or a woody plant or a derivative thereof functionally associated to the nanoparticle core. Some embodiments provide for wood products and wood treatment compositions including such capped nanoparticles, and methods for preparing and using such capped nanoparticles to produce treated wood or treated wood products.

23 Claims, No Drawings

NON-COVALENTLY BONDING ANTI-MICROBIAL NANOPARTICLES FOR WATER SOLUBLE WOOD TREATMENT

CLAIM OF PRIORITY

This application is a national phase application under 35 U.S.C. §371 of International Application No. PCT/US2011/041372, filed Jun. 22, 2011, which is incorporated herein by reference in its entirety.

BACKGROUND

Wood is degraded by microorganisms, particularly fungi and bacteria, which contribute to degradation by creating environmental conditions favorable to further decay or consumption by larger organisms, such as insects or marine borers. Wood preservation methods attempt to arrest degradation by these microorganisms. Current and near term wood preservation techniques suffer from limitations such as wood treatability, broad spectrum efficacy, affordability, and environmental safety/human toxicity. For example, some of the most effective treatments use arsenic containing compounds such as chromated copper arsenate (CCA) and may no longer be used in much of the world because of potential toxicity/environmental concerns. In addition, certain fungi have developed resistance to copper compounds.

Wood preservatives traditionally are classified as either oil-borne or waterborne depending on the type of solvent used. Waterborne preservatives are generally easy to apply, but leaching lowers efficacy of waterborne preservatives and increases environmental/safety burden. For example, boron-based waterborne preservatives are cheap and effective but leach easily, and some boron preservatives only rate for extremely narrow uses. Chromates, commonly used in wood preservatives, provide increased retention; however, chromates increase heavy metal toxicity of the preservative.

A water-soluble chemical formulation with a broad spectrum efficacy and high retention in the wood after application would provide a highly desirable preservative. According to the U.S. Department Of Agriculture's Forest Products Laboratory, wood preservatives must meet two broad criteria: "(1) they must provide the desired wood protection in the intended end use [i.e. efficacy in the end application], (2) they must do so without presenting unreasonable risks to people or the environment." The embodiments described herein provide water-soluble, high retention, safe, and broad spectrum wood preservatives for multiple applications.

SUMMARY

Some embodiments described herein are directed to a capped nanoparticle having a nanoparticle core and a capping agent including at least one biochemical constituent of a woody plant or a derivative thereof functionally associated with the nanoparticle core.

Other embodiments are directed to a wood product including a wood-containing material and at least one capped nanoparticle having (a) a nanoparticle core and (b) a capping agent including at least one biochemical constituent of a woody plant or a derivative thereof functionally associated with the nanoparticle core.

Still other embodiments are directed to a wood treatment composition including a solvent and at least one capped nanoparticle suspended in the solvent wherein the capped nanoparticle has (a) a nanoparticle core; and (b) a capping agent including at least one biochemical constituent of a woody plant or a derivative thereof functionally associated with the nanoparticle core.

Further embodiments are directed to a method for treating a wood product, the method includes the steps of providing an untreated material comprising wood or a wood product, providing a wood treatment composition including a solvent and at least one capped nanoparticle suspended in the solvent, wherein the capped nanoparticle has (a) a nanoparticle core and (b) a capping agent including at least one biochemical constituent of a woody plant or a derivative thereof functionally associated with the nanoparticle core, and contacting the untreated material and the wood treatment composition to form a treated material.

Yet other embodiments are directed to a method for preparing a capped nanoparticle, the method including the steps of combining (a) at least one nanoparticle precursor, (b) at least one reducing agent, and (c) at least one capping agent having at least one biochemical constituent of woody plant or derivatives thereof, in a solvent to form a mixture and heating the mixture.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Various embodiments are directed to capped nanoparticles having a nanoparticle core that can provide broad spectrum anti-microbial and anti-fungal activity and a capping agent that includes at least one biochemical constituent of wood or a derivative thereof. In some embodiments, the capping agent is functionally associated with the core nanoparticle. These capped nanoparticles may be used in the treatment of wood and wood products to provide wood treatment compositions with broad spectrum anti-microbial and anti-fungal properties while being resistant to leaching. Such treatment compositions may, therefore, be more effective for providing long term anti-microbial and anti-fungal preservative activity while being safer, and having less environmental impact than many currently available wood treatment compositions. Accordingly, some embodiments herein are directed to wood treatment compositions including capped nanoparticles as described above, methods for treating wood and wood products with these wood treatment compositions, and the wood and wood products so treated in which the capped nanoparticles of various embodiments are incorporated.

Embodiments are not limited by the biochemical constituents of wood that are incorporated into the capping agents, and in some embodiments, the capping agent may be at least one of the polysaccharides that make up the bulk of natural wood including, but not limited to, pectins, hemicelluloses, celluloses, lignins, pectins, callose, glycoproteins, arabinogalactan proteins, and combinations thereof. In other embodiments, the capping agent may be enzymes, proteins, and other carbohydrates associated with wood and woody plants. In still other embodiments, at least one polysaccharide may be combined with at least one enzyme, protein, or other carbohydrate to provide a capping agent having more than one constituent.

Without wishing to be bound by theory, nanoparticles capped with these biochemical constituents are absorbed into wood during treatment and bind non-covalently with the molecular components of the wood being treated. These non-covalent interactions may increase retention of the nanoparticles in the wood and improve the preservative function of the treatment. In addition, the non-covalent bonds between the capping agent and the wood minimize leaching making the nanoparticles environmentally safer than uncapped nanoparticles and/or other treatments that may have higher leaching tendencies.

Embodiments are not limited to any particular type of nanoparticle core, and the nanoparticle cores of various embodiments may be inorganic or metallic. In some embodiments, the capped nanoparticle may be anti-microbial. In some embodiments, the nanoparticle cores may be anti-microbial nanoparticles that provide, for example, anti-bacterial, anti-viral, or other antibiotic activity. In other embodiments, the nanoparticle cores may have anti-fungal activity. In still other embodiments, nanoparticle cores having different activities may be combined into a single wood treatment composition. For example, a wood treatment composition may include nanoparticle cores that exhibit a particular anti-microbial activity and at least one other nanoparticle core that exhibits a different anti-microbial activity and/or anti-fungal activity. These nanoparticle cores can be capped with the same or different capping agents. Such wood treatment compositions would provide broad spectrum preservative activity with good retention in the wood. In certain embodiments, the nanoparticle cores may be generally recognized as safe (GRAS) chemicals such as, for example, ZnO.

The nanoparticle cores of some embodiments may be metallic and can be composed of metals, metal alloys, metal oxides, or combinations thereof. In some embodiments, the nanoparticle cores may be bare metal nanoparticles composed of, for example, Zn, Cu, Ag, Pt, and the like and combinations thereof, and in certain embodiments, the metal nanoparticles may be silver (Ag), which has well characterized anti-microbial activity. In some embodiments, the nanoparticle cores may be composed of metal oxides such as, for example, MgO, ZnO, FeO, $Fe_3O_4$, ZnS, CuO, $SnO_2$, $TiO_2$, $AgNO_3$, and combinations thereof, and in particular embodiments, the nanoparticle cores may be composed of ZnO, MgO, CaO, and combinations thereof, which have well-known anti-fungal and anti-bacterial activity. In some embodiments, the nanoparticle cores used in the wood treatment compositions may be a combination of any of the various types or kinds of nanoparticle cores described above. In one exemplary embodiment, commercially available ZnO nanoparticle cores, which have anti-fungal activity and which can be obtained in hydrophilic and hydrophobic forms, can be used as the base nanoparticle core. ZnO nanoparticle cores have been shown to be effective in admixtures, as an additive, or in immobilized forms, and hydrophilic bare ZnO nanoparticle cores may be particularly for use in waterborne wood treatment compositions.

The nanoparticle cores can generally have any size and shape. Nanoparticle cores are typically spherical, but can be cylindrical, oblong, or other shapes as well. Example core size ranges include about 1 nm to about 250 nm, or about 5 nm to about 150 nm. Specific examples of the core size include about 1 nm, about 5 nm, about 10 nm, about 50 nm, about 100 nm, about 125 nm, about 150 nm, about 175 nm, about 200 nm, about 225 nm, about 250 nm, and ranges between any two of these values.

Because the nanoparticle cores are typically not well retained in wood and exhibit little resistance to leaching, leading to lower efficacy and high environmental/safety burden, nanoparticle cores such as those described above can be functionalized, or capped, with biochemical constituents of wood or woody plants or derivatives thereof. The biochemical constituents can provide non-covalent interactions with wood being treated, which effectively bind the nanoparticle cores to the treated wood increasing the retention of the capped nanoparticle in the wood when compared to the nanoparticles core alone, thereby reducing leaching and improving the environmental/safety burden of the treated wood and simultaneously improving efficacy and/or longevity of the treatments.

Any biochemical constituent of wood can be used as a capping agent. The components of wood and woody plants are well known, and the biochemical constituents of wood may be easily obtained either by isolating the various constituents from natural wood through known methods or from commercial vendors. For example, biochemical constituents of wood such as whole cellulose, hemicellulose, pectins, complex mixtures of components, and/or individual components/residues such as xyloglucans may be obtained from natural wood by biochemical or chemical digestions. The resulting complex mixtures of the biochemical components may then be further purified to isolate individual constituents of the wood. Techniques for purifying individual biochemical constituents of wood from wood and wood pulp are well known in the wood chemistry art.

The primary biochemical constituents of wood include: cellulose, which is a linear (unbranched) polymer of beta-1,4-linked D-glycosyl residues (polysaccharides); hemicellulose, which is a non-linear (branched) polymer of diverse polysaccharides including, for example, xyloglucans, non-linear (branched) beta-1,4-linked glycosyl residues, which may include alpha-D-xylosyl and D-galactosyl and L-arabinosyl alpha-L-fucosyl residues, and xylans, beta-1,4-D-xylosyl chains, which can include 4-O-methyl-glucuronyl, glucuronyl, acetyl and arabinose substitutions; mannans and other monomers; lignins, which are generally aromatic and hydrophobic and include macromolecules of monolignol monomers such as p-coumaryl alcohol, coniferyl alcohol, and sinapyl alcohol that can be methoxylated; pectins, which include complex polysaccharides including, for example, homogalacturonans, substituted galacturonans, and rhamnogalacturonans and contain 1,4-linked beta-D-galactosyluronic acids; or other components of woody plants including, but not limited to, callose (a triple helix of linear predominately beta-1,3-linked D-glucosyl), glycoproteins, arabinogalactan proteins (AGPs), and enzymes. Any of these components and mixtures of these components may be used as capping agents.

Cellulose, hemicelluloses, lignins, and pectins make up the primary mass of wood and serve as the primary substrates for many degradative micro-organisms. The large number of hydroxyl and other dentate groups of these constituents facilitate non-covalent interactions such as hydrogen bonding between components of the same type and between different components. Within these systems, the individual molecular components sometimes have well-defined, well-described interactions. For example, xyloglucans in hemicelluloses tether to cellulose and, since xyloglucans are one of the most abundant components of hemicelluloses, contribute highly to hemicellulose-to-cellulose binding. Hemicellulose-to-pectin non-covalent bonding forms a matrix in which cellulose microfibrils embed themselves in secondary cell woods. These non-covalent associations between the constituents are very strong and, in some cases, are responsible for the structural stability of the wood cell, microfibrils, or even wood as a whole. Without wishing to be bound by theory, the biochemical constituents of wood included in the capping agent may be chosen to provide specific interactions with specific components of the wood being treated. Selecting specific biochemical constituents that are included in the capping agent allows for wood treatment compositions that are specifically designed for particular types or species of wood based on the biochemical make up of that particular species. For example, a lignin capping agent may increase lignin interaction, which may provide a more efficacious treatment for woods with high lignin content.

In some embodiments, the biochemical constituent of wood included in the capping agent may be modified or derivatized, and in some embodiments, the biochemical constituents or a portion of the biochemical constituents of the wood included in the capping agent may be modified to modulate hydrophilicity, hydrophobicity, and/or affinity for specific wood molecules. For example, in some embodiments, cellulose can be partially or wholly converted to esters or ethers to modulate hydrophilicity or hydrophobicity. Without wishing to be bound by theory, modifying the biochemical constituents in the capping agent may provide a capping agent that is more easily integrated into waterborne wood treatment compositions and can be more efficiently distributed throughout the wood during treatment. Increasing hydrophilicity may also increase specific interactions or the number of specific interactions within the treated wood. For example, as discussed above, esterification of cellulose increases hydrophilicity. In addition, esterification of cellulose can induce branching, which may increase the effective surface area for interactions and the number of interactions between the capping agent and the nanoparticle core and/or the number of interactions between the capping agent and the wood during treatment. Hydrophilicity and hydrophobicity can also be modulated by providing mixtures of different biochemical constituents of wood in the capping agent in particular ratios. For example, xyloglucan molecules can be included in a capping agent that also includes lignin to increase the overall hydrophobicity of the capped nanoparticle, which increases lignin interactions improving the efficacy of treatment of woods with high lignin content.

In some embodiments, the biochemical constituents of wood and derivatives thereof and modified biochemical constituents of wood or mixtures thereof used as a capping agent can associate with the nanoparticle core directly through interactions between the dentate groups of the biochemical constituent, such as hydroxyl, carbonyl, ester, amine, and/or carboxylic acid groups and an outer surface of the nanoparticle core. In such embodiments, the dentate groups may form non-covalent interactions with the outermost surface of the nanoparticle core. In other embodiments, coordination complexes may form on the surface of the nanoparticle cores in which the dentate group and at least one metal atom on the surface of the nanoparticle share electrons. In still other embodiments, various dentate groups on the biochemical constituent of wood may be associated with the nanoparticle core through a combination of non-covalent interactions and coordination complexes.

In other embodiments, the capped nanoparticle core may include a linker interposed between the biochemical constituent of the wood and the nanoparticle core that forms an attachment between the nanoparticle core and the capping agent. Various linkers are known and used in the art and are encompassed by embodiments of the invention. In one exemplary embodiment, the linker may be polyvinylpyrrolidone (PVP), which includes pyrrolidone moieties having heterocycle nitrogen atoms that can bind to the outermost surface of the nanoparticle core. The pyrrolidone moieties and/or vinyl groups (—CH═CH—) of linkers such as PVP can also react with the capping agent to form a covalent link with the capping agent thereby attaching the capping agent to the nanoparticle core. Other linkers include, but are not limited to, dithiolate, polyethylene glycol and polyethylene glycol derivatives, nucleic acids including deoxyribonucleic acid (DNA) and ribonucleic acid (RNA), peptides, and other biomolecules and biomolecule derivatives, epoxy amines, and combinations thereof.

In some embodiments, a linker can be attached to the nanoparticle core before the capping agent is reacted with the linker to bind the capping agent to the nanoparticle core. In other embodiments, the biochemical constituent of wood can be modified to include a linker and/or moieties that are highly reactive with the surface of nanoparticle cores such as, for example, pyrrolidines, pyrroles, imidazoles, thiazoles, and the like. The capping agent, in such embodiments, may include a biochemical constituent of wood covalently associated with a linker. This capping agent can then be associated the with nanoparticle core. Without wishing to be bound by theory, linkers can increase coupling efficiency, which can provide a greater concentration of capping molecules associated with each individual nanoparticle core thereby increasing accessible surface area of biochemical constituent of wood on the nanoparticle core and the number or potential number of interactions between the capping agent and components of the wood being treated. Increasing the concentration of capping agents associated with the nanoparticle cores may also improve the compatibility of the nanoparticle in the wood during treatment.

In further embodiments, the biochemical constituents of the wood or derivatives thereof or modified biochemical constituents can be crosslinked after being associated with the nanoparticle core. Crosslinking provides intra capping agent bonds that may further enhance the stability of the interactions between the capping agent and the nanoparticle core, thereby further enhancing the preservative activity of the treatment over time by reducing leaching.

Some embodiments are also directed to methods for preparing capped nanoparticle cores, and such embodiments generally include the steps of providing a nanoparticle core, providing a capping agent including at least one biochemical constituent of a woody plant or a derivative of a biochemical constituent of a woody plant and functionally associating the biochemical constituent with the nanoparticle core. Chemical procedures for capping core nanoparticles with organic capping agents are well known in the art. For example, in some embodiments, at least one capping agent can be combined with nanoparticle precursors during synthesis of the nanoparticle and/or a substitution reaction is performed after nanoparticle cores have been formed. Examples of organic capping agents include, but are not limited to, starches (chains of saccharides), lipids, and dextrins. Similarly, polymers that can be used as linkers including, but not limited to, poly (vinylpyrrolidone) (PVP) can be associated with nanoparticle cores by known techniques, and organic capping agents are reacted with the linkers to provide capped nanoparticle cores.

In particular exemplary embodiments, the methods of the invention may include the steps of combining at least one nanoparticle precursor, at least one reducing agent, and at least one capping agent, in which the capping agent includes at least one biochemical constituent of woody plant or a derivative thereof in a solvent to form a mixture and heating the mixture. The solvent may be an organic solvent, water, an aqueous solution, and in some embodiments, a combination of an aqueous solution and an organic solvent. In some embodiments, the step of combining may include separate steps of combining at least one nanoparticle precursor and at least one reducing agent in a solvent to form a first mixture and combining at least one biochemical constituent of wood or a woody plant or derivatives thereof in a solvent to form a second mixture. These first and second mixtures may then be combined into the mixture that is heated. In such embodiments, the first mixture may be heated and the second mixture may be combined into the second mixture during heating. Heating may be carried out at any temperature known in the art for the preparation of nanoparticle cores, and in certain embodiments, the heating may be carried out at a temperature of from about 50° C. to about 200° C., or about 20° C. to about 100° C. Specific examples of temperature include about 50° C., about 75° C., about 100° C., about 125° C., about 150° C., about 175° C., about 200° C., and ranges between any two of these values.

Nanoparticle precursors are well known in the art, and any type of nanoparticle precursor known in the art can be used in connection with the methods described above. In particular embodiments, the nanoparticle precursors may be organometallic compounds, inorganic salts, coordination compounds, and combinations thereof. For example, in some embodiments, nanoparticle precursors may be Mg, Zn, Fe, Cu, Sn, Ti, Ag, and combinations thereof, or salts of thereof.

The capping agent is an outer-most layer of a capped nanoparticle formed in the methods described herein and can be any of the capping agents described above including, but not limited to, cellulose, hemicellulose, lignins, pectins, callose, glycoproteins, arabinogalactan proteins, enzymes, and combinations thereof. In some embodiments, the capping agent may be modified to increase the hydrophobicity or hydrophilicity by, for example, increasing the number of esters or branching in the capping agent constituents or providing a linker that may improve binding between the capping agent and the nanoparticle core.

In still other embodiments, such methods may further include the steps of monitoring an average size of the nanoparticle cores formed in the mixture and terminating nanoparticle core formation when the average nanoparticle core size reaches a predetermined value such as, for example, about 1 nm to about 250 nm or about 5 nm to about 150 nm. Specific examples of the core size include about 1 nm, about 5 nm, about 10 nm, about 50 nm, about 100 nm, about 125 nm, about 150 nm, about 175 nm, about 200 nm, about 225 nm, about 250 nm, and ranges between any two of these values.

The capped nanoparticle cores have capping agents that include biochemical constituents of wood such as, for example, cellulose, hemicellulose, pectins, lignins, xyloglycans, and mixtures of these as described above may be incorporated into wood treatment compositions that may include a solvent. In some embodiments, the solvent may be water or an aqueous solution providing a waterborne wood treatment composition, and in other embodiments, the solvent may be, for example, creosote, linseed oil, sunflower seed oil, grape seed oil, white spirits, kerosene, and combinations thereof to provide a oil-borne wood treatment composition.

In other embodiments, additional components that facilitate impregnation of the nanoparticles into the wood may be included in the solvent. For example, acid/base addition can be used to modulate the formulation pH, which is known to affect impregnation ability in wood treatment systems such as copper containing systems. Further additional components may be provided in the wood treatment compositions as well. For example, in some embodiments, the wood treatment composition may include other anti-fungal, anti-bacterial, anti-viral, or other antibiotic agents, and in other embodiments, the wood treatment may include additives that reduce leaching, provide color, or facilitate handling of the treatment composition.

The wood treatment compositions described above may be used alone by simply contacting wood or a wood product with the wood treatment composition. For example, in some embodiments, the wood treatment composition may be applied directly to wood or a wood product by, for example, brushing on; and allowed to dry. In other embodiments, the capped nanoparticle cores or a wood treatment composition including capped nanoparticle cores may be incorporated into a wood finishing product such as, for example, wood stains or paints. These products may be applied as is known in the art by, for example, immersing, brushing, spraying, wiping, or rolling on and allowing to dry. The nanoparticle cores and/or a portion of the solvent of the wood treatment composition may be absorbed by the wood thereby providing treatment and preservatives to the wood or wood product.

In other embodiments, the wood treatment compositions described above may be used in a wood treatment process such as, for example, pressure treating. Pressure methods are well known and used in the art. For example, various treatment regimens, such as those used for impregnation of copper naphthalene and other copper reagents may be used for impregnation of wood treatment compositions including capped nanoparticle cores and may be easily adapted to use the wood treatment compositions of the invention. Pressure treating wood or wood products may be carried out by contacting the wood or a wood product with a wood treatment composition that at least includes a solvent and nanoparticle cores capped with at least one biochemical constituent of a woody plant or derivatives thereof and applying pressure to wood saturated with the mixture. The amount of pressure applied may vary depending on the protocol used. For example, the pressure may be from about 150 psi (10.2 atm) to about 250 psi (17.0 atm). In some embodiments, the treating may be carried out at room temperature, and in other embodiments, the treatment process may further include the step of heating the wood or wood product saturated with the wood treatment composition. Pressure and/or heating can be carried out for at least about 1 hour or more, and following pressure and/or heating any unabsorbed wood treatment composition can be removed from the wood or wood product. In some embodiments, the treatment methods may further include applying vacuum to the wood or wood product to further remove excess liquid. In certain embodiments, the vacuum may be a relatively strong vacuum having a pressure of, for example, at least less than 100 mbar.

The processes and methods described above may be applied or used to treat any type of wood product available. For example, in various embodiments, the wood or wood product may be natural wood, cut wood, landscaping timbers, solid board, plywood, engineered wood, particle board, medium density fiber board, and oriented strand board. In other embodiments, the wood or wood product may be wood pulp that can be used to make particle and fiber boards or that are incorporated into paper and paper products such as, for example, stock paper and cardboard. Thus, further embodiments may include wood products such as, for example, natural wood, cut wood, landscaping timbers, solid board, plywood, engineered wood, particle board, medium density fiber board, and oriented strand board including capped nanoparticle cores described above. In certain embodiments, the wood or wood product may be treated before the treatment processes and method described herein are carried out. For example, the wood or wood product may be pretreated by drying, pressure treatment, acetylation, boron treatment, and combinations thereof.

Embodiments described herein provide a broadly applicable system including anti-microbial and anti-fungal nanoparticle cores capped with endogenous wood components that can interact and non-covalently bind to wood or wood products after treatment. The treatments and methods use low cost components such as ZnO and complex mixtures of wood, and separation of the anti-microbial/anti-fungal and wood-interacting components in a single treatment allow for tailoring of the treatment nanoparticle cores for specific applications. For example, woods having higher lignin content can be treated with particles having high lignin capping agents. Such capped nanoparticle cores and methods are not amenable to current treatments.

In one exemplary embodiment, capped ZnO nanoparticle cores can be produced similarly to starch, dextran, or PVP capped nanoparticle cores. The US FDA considers ZnO a GRAS compound with broad-spectrum anti-fungal properties. This makes ZnO an excellent choice as the basis for a wood treatment. For example, hydrolyzation of $Zn(Ac)_2 \, H_2O$ can be carried out in a basic methanol solution in the presence of xyloglucans. The dentate properties of xyloglucans induce nanoparticle capping by attaching to the outer surface of the nanoparticle cores. An excess of xyloglucan can be used for complete coverage, or a monolayer of xyloglucan can be produced by using reagent-limiting amounts of xyloglucan. Such methods may be carried using such schemes for other, similar, dentate compounds.

These capped nanoparticle cores can be loaded into wood by pressure treatment, similar to copper naphthenate or other water-borne preservatives. For example, a solution including the capped nanoparticle cores may be used to saturate the wood, and a pressure of 180 psi to 200 psi may be applied at room temperature for an hour or longer (dependent on the size and dimensions of the wood).

EXAMPLES

Example 1

Zinc Oxide Nanoparticle Core Capped with Xyloglucan $Zn(Ac)_2 \, H_2O$ may be dissolved in a solution of 200 ml of methanol and 6 ml of distilled water. Nitrogen may be introduced into the mixture for about 20 minutes, and the solution may be stirred in an inert environment for 2 hours. Purified xyloglucan may then be added to the mixture, and stirring in an inert environment may be continued overnight. The solution may be filtered to remove the capped nanoparticles produced from the solution, and the filtered nanoparticles may be washed in methanol and filtered again. The washing and filtering step may be repeated if desired. The filtered capped nanoparticles may be dried in a dehydrator to produce a powder of ZnO nanoparticle cores capped with xyloglucan.

Example 2

Zinc Oxide Nanoparticle Core Capped with Lignin $Zn(Ac)_2 \, H_2O$ may be dissolved in a solution of 200 ml of methanol and 6 ml of distilled water. Nitrogen may be introduced into the mixture for about 20 minutes, and the solution may be stirred in an inert environment for 2 hours. Purified lignin may then be added to the mixture, and stirring in an inert environment may be continued overnight. The solution may be filtered to remove the capped nanoparticles produced from the solution, and the filtered nanoparticles may be washed in methanol and filtered again. The washing and filtering step may be repeated if desired. The filtered capped nanoparticles may be dried in a dehydrator to produce a powder of ZnO nanoparticle cores capped with lignin.

Example 3

Zinc Oxide Nanoparticle Core Capped with a Complex Mixture $Zn(Ac)_2 \, H_2O$ may be dissolved in a solution of 200 ml of methanol and 6 ml of distilled water. Nitrogen may be introduced into the mixture for about 20 minutes, and the solution may be stirred in an inert environment for 2 hours. A mixture of wood constituents including cellulose, hemicelluloses, and lignin prepared by enzymatically treating dried sawdust may then be added to the mixture, and stirring in an inert environment may be continued overnight. The solution may be filtered to remove the capped nanoparticles produced from the solution, and the filtered nanoparticles may be washed in methanol and filtered again. The washing and filtering step may be repeated if desired. The filtered capped nanoparticles may be dried in a dehydrator to produce a powder of ZnO nanoparticle cores capped with a mixture of wood constituents.

Example 4

Copper Oxide Nanoparticle Core Capped with Xyloglucan $Cu(OAc)_2(H_2O)_2$ may be dissolved in a solution of 200 ml of methanol and 6 ml of distilled water. Nitrogen may be introduced into the mixture for about 20 minutes, and the solution may be stirred in an inert environment for 2 hours. Purified xyloglucan may then be added to the mixture, and stirring in an inert environment may be continued overnight. The solution may be filtered to remove the capped nanoparticles produced from the solution, and the filtered nanoparticles may be washed in methanol and filtered again. The washing and filtering step may be repeated if desired. The filtered capped nanoparticles may be dried in a dehydrator to produce a powder of CuO nanoparticle cores capped with xyloglucan.

Example 5

Copper Oxide Nanoparticle Core Capped with a Complex Mixture $Cu(OAc)_2(H_2O)_2$ may be dissolved in a solution of 200 ml of methanol and 6 ml of distilled water. Nitrogen may be introduced into the mixture for about 20 minutes, and the solution may be stirred in an inert environment for 2 hours. A mixture of wood constituents including cellulose, hemicelluloses, and lignin prepared by enzymatically treating dried sawdust may then be added to the mixture, and stirring in an inert environment may be continued overnight. The solution may be filtered to remove the capped nanoparticles produced from the solution, and the filtered nanoparticles may be washed in methanol and filtered again. The washing and filtering step may be repeated if desired. The filtered capped nanoparticles may be dried in a dehydrator to produce a powder of CuO nanoparticle cores capped with a mixture of wood constituents.

Example 6

Preparation of a Wood Treatment Composition 155 grams of 28%-30% ammonium hydroxide solution (28%-30% $NH_3$) and 0.15 moles of organic acid (i.e. 6 g formic acid, 8 g acetic acid, 9 g propionic acid, or 27 g citric acid) may be mixed with 160 grams of deionized water. 70 grams of any of the capped ZnO nanoparticles described in Examples 1-3 may be added and mixed with the solution to produce a concentrate. The concentrates may be diluted and sodium tetraborate pentahydrate may be added and dissolved to produce a final treatment solution containing 1.5% by weight sodium tetraborate pentahydrate (2% borax decahydrate equivalent) and 0.75% zinc oxide (ZnO) equivalent.

Example 7

Pressure Treatment of Cut Wood

Two 5.5×5.5×1 inch (14×14×2.5 cm) pieces of Southern Yellow Pine may be loaded into a 2 L pressure vessel equipment with an inlet tube, gas/vacuum inlet, pressure sensors, dropout valve and level indicators. The vessel may be sealed and the pressure may be reduced to 26-27 inches of Hg (88-91 kPa) and held for 15-20 minutes. The vacuum may be turned off, and the treatment solution described in Example 4 may be drawn into the vessel to completely cover the wood. The vessel may be pressurized to approximately 150 psig (1136 kPa). A pump may be used to maintain the liquid level above the wood. When no more treatment solution is taken up by the wood, the pressure may be released and the vessel drained via the dropout valve. The wood may be removed or a vacuum may be pulled on the vessel again for approximately 5 minutes, the vessel again drained and then the wood removed to partially remove some of the surface moisture from the treated wood.

Example 8

Vacuum Treatment of Cut Wood

One piece of 5.5×5.5×1 inch Southern Yellow Pine may be placed in a vacuum desiccator, weighted down with a stainless steel bolt to prevent it from floating and put under vacuum, 25-27 inches of Hg (85-91 kPa), and held for 15-30 minutes. Enough treatment solution may be added to fully cover the wood while the wood is under vacuum. The vacuum soak may be held for 30-60 minutes, then the vacuum may be released and the wood may be soaked in the treatment solution at atmospheric pressure for an additional 15-30 minutes before removal.

The illustrative embodiments described in the detailed description and claims are not meant to be limiting. Other embodiments may be utilized, and other changes may be made, without departing from the spirit or scope of the subject matter presented herein. It will be readily understood that the aspects of this disclosure, as generally described herein, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "at least one" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "at least one" or "at least one" and indefinite articles such as "a" or "an" (e.g., "a" and/or "an" should be interpreted to mean "at least one" or "at least one"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A wood product comprising:
a wood-containing material; and
at least one capped nanoparticle functionally associated with the wood-containing material through at least one non-covalent force, the capped nanoparticle comprising:
a nanoparticle core; and
a capping agent comprising at least one biochemical constituent of a woody plant or a derivative thereof functionally associated with the nanoparticle core.

2. The wood product of claim 1, wherein the wood-containing material is selected from the group consisting of natural wood, cut wood, landscaping timbers, solid board, plywood, engineered wood, particle board, medium density fiber board, and oriented strand board.

3. The wood product of claim 1, wherein the capping agent is selected from the group consisting of polysaccharides, cellulose, hemicellulose, lignins, pectins, callose, glycoproteins, arabinogalactan proteins, enzymes, and combinations thereof.

4. The wood product of claim 1, wherein the capping agent is modified to increase or decrease the affinity of the capping agent for wood or wood components or increase the capping agents hydrophobicity or hydrophilicity.

5. The wood product of claim 1, wherein the nanoparticle core comprises Zn, Cu, Ag, Pt, MgO, ZnO, FeO, $Fe_3O_4$, ZnS, CuO, $SnO_2$, $TiO_2$, $AgNO_3$, or combinations thereof.

6. A wood treatment composition for treating a wood product, the composition comprising:
a solvent; and
at least one capped nanoparticle suspended in the solvent, wherein the capped nanoparticle comprises:
a nanoparticle core; and
a capping agent functionally associated with the nanoparticle core, the capping agent comprising at least one biochemical constituent of a woody plant or a derivative thereof configured to functionally associate with the wood product through at least one non-covalent force.

7. The wood treatment composition of claim 6, wherein the capping agent is selected from the group consisting of polysaccharides, cellulose, hemicellulose, lignins, pectins, callose, glycoproteins, arabinogalactan proteins, enzymes, and combinations thereof.

8. The wood treatment composition of claim 6, wherein the capping agent is modified to increase or decrease the affinity of the capping agent for wood or wood components or increase the capping agents hydrophobicity or hydrophilicity.

9. The wood treatment composition of claim 6, wherein the nanoparticle core comprises Zn, Cu, Ag, Pt, MgO, ZnO, FeO, $Fe_3O_4$, ZnS, CuO, $SnO_2$, $TiO_2$, $AgNO_3$, or combinations thereof.

10. The wood treatment composition of claim 6, wherein the solvent is selected from the group consisting of water, creosote, linseed oil, sunflower seed oil, grape seed oil, white spirits, kerosene, and combinations thereof.

11. A method for treating a wood product, the method comprising:
providing an untreated material comprising wood or a wood product;
providing a wood treatment composition comprising:
a solvent; and
at least one capped nanoparticle suspended in the solvent, wherein the capped nanoparticle comprises;
a nanoparticle core; and
a capping agent functionally associated with the nanoparticle core, the capping agent comprising at least one biochemical constituent of a woody plant or a derivative thereof configured to functionally associate with the wood or wood product through at least one non-covalent force; and
contacting the untreated material and the wood treatment composition to functionally associate the capped nanoparticles with the wood or wood product through at least one non-covalent force to form a treated material.

12. The method of claim 11, wherein the nanoparticle core comprises Zn, Cu, Ag, Pt, MgO, ZnO, FeO, $Fe_3O_4$, ZnS, CuO, $SnO_2$, $TiO_2$, $AgNO_3$, or combinations thereof.

13. The method of claim 11, wherein the capping agent is selected from the group consisting of polysaccharides, cellulose, hemicellulose, lignins, pectins, callose, glycoproteins, arabinogalactan proteins, enzymes, and combinations thereof.

14. The method of claim 11, wherein the method further comprises heating the treated material.

15. The method of claim 11, wherein the contacting is carried out at room temperature.

16. The method of claim 11, further comprising applying vacuum to the treated material.

17. The method of claim 11, wherein the wood or wood product is selected from the group consisting of natural wood, cut wood, landscaping timbers, solid board, plywood, engineered wood, particle board, medium density fiber board, and oriented strand board.

18. The wood product of claim 1, wherein the nanoparticle core is configured to provide at least one of anti-microbial activity and anti-fungal activity.

19. The wood product of claim 1, further comprising at least one linker disposed between and bonding the nanoparticle core with the capping agent.

20. The wood product of claim 19, wherein the linker comprises polyvinylpyrrolidone, dithiolate, polyethylene glycol and polyethylene glycol derivatives, nucleic acids including deoxyribonucleic acid (DNA) and ribonucleic acid (RNA), peptides, and other biomolecules and biomolecule derivatives, epoxy amines, and combinations thereof.

21. The wood product of claim 1, wherein the capping agent comprises two or more biochemical constituents of a woody plant or derivatives thereof.

22. The wood treatment composition of claim 6, wherein the nanoparticle core is configured to provide at least one of anti-microbial activity and anti-fungal activity.

23. The method of claim 11, wherein the nanoparticle core is configured to provide at least one of anti-microbial activity and anti-fungal activity.

* * * * *